(12) United States Patent
Vahey et al.

(10) Patent No.: US 8,536,529 B2
(45) Date of Patent: Sep. 17, 2013

(54) NON-CONTACT SURFACE CHEMISTRY MEASUREMENT APPARATUS AND METHOD

(75) Inventors: Paul Griffin Vahey, Seattle, WA (US); Gregory James Werner, Puyallup, VT (US); Paul H. Shelley, Lakewood, WA (US)

(73) Assignee: The Boeing Company, Chicago, IL (US)

( * ) Notice: Subject to any disclaimer, the term of this patent is extended or adjusted under 35 U.S.C. 154(b) by 319 days.

(21) Appl. No.: 12/903,548

(22) Filed: Oct. 13, 2010

(65) Prior Publication Data

US 2012/0092665 A1 Apr. 19, 2012

(51) Int. Cl.
*G01N 21/35* (2006.01)

(52) U.S. Cl.
USPC .................................................... 250/339.11

(58) Field of Classification Search
USPC .................................................... 250/339.11
See application file for complete search history.

(56) References Cited

U.S. PATENT DOCUMENTS

| 6,697,155 | B2 * | 2/2004 | Dobbs et al. .................. 356/300 |
| 6,784,431 | B2 | 8/2004 | Shelley |
| 6,794,651 | B2 | 9/2004 | Shelley et al. |
| 6,903,339 | B2 | 6/2005 | Shelley |
| 6,906,327 | B2 | 6/2005 | Shelley |
| 7,115,869 | B2 | 10/2006 | Shelley |
| 7,223,977 | B2 | 5/2007 | Shelley |
| 7,236,243 | B2 * | 6/2007 | Beecroft et al. ............... 356/328 |
| 7,796,251 | B2 * | 9/2010 | Ponsardin et al. ............. 356/301 |
| 2004/0135085 | A1 | 7/2004 | Trofimov et al. |
| 2005/0264808 | A1 | 12/2005 | Wang |
| 2006/0263252 | A1 | 11/2006 | Sanchez-Olea et al. |
| 2007/0194239 | A1 * | 8/2007 | McAllister et al. ....... 250/339.07 |
| 2008/0076983 | A1 | 3/2008 | Debreczeny et al. |
| 2008/0144677 | A1 | 6/2008 | Belkin et al. |
| 2009/0249521 | A1 | 10/2009 | Dazzi et al. |

FOREIGN PATENT DOCUMENTS

JP 2003254856 A 9/2003

OTHER PUBLICATIONS

International Searching Authority, Invitation to Pay Additional Fees and Partial Search Report for PCTUS2011/049331 dated Nov. 2, 2011.

* cited by examiner

*Primary Examiner* — Constantine Hannaher
(74) *Attorney, Agent, or Firm* — Parsons Behle & Latimer

(57) ABSTRACT

A surface chemistry measuring apparatus includes a processor, an array of tunable infrared laser spectrometers interfacing with the processor and configured for simultaneous measurement of surface chemistry across a surface to be measured using a range of infrared wavelengths and a display interfacing with the processor and adapted to display IR spectra of infrared wavelengths reflected from the surface to be measured.

20 Claims, 3 Drawing Sheets

NON-CONTACT SURFACE CHEMISTRY MEASUREMENT APPARATUS AND METHOD

TECHNICAL FIELD

The disclosure generally relates to measurement of contamination or other surface chemistry on the surface of a structure such as a composite structure. More particularly, the disclosure relates to a non-contact surface chemistry measurement apparatus and method which does not require physical contact with the surface being tested.

BACKGROUND

Current methods of detecting contaminants or other surface chemistry on the surface of a composite structure or other structure may include the use of IR spectroscopy. However, conventional IR spectroscopy technology may not have the sensitivity to measure changes in surface chemistry or low levels of contamination that can impact the quality of a structural bond. Since they require contact with a surface during measurement, current IR spectroscopy methods may introduce additional contaminants onto the surface.

SUMMARY

The disclosure is generally directed to a surface chemistry measuring apparatus. An illustrative embodiment of the surface chemistry measuring apparatus includes a processor, an array of tunable infrared laser spectrometers interfacing with the processor and configured for simultaneous measurement of surface chemistry across a surface to be measured using a range of infrared wavelengths and a display interfacing with the processor and adapted to display IR spectra of infrared wavelengths reflected from the surface to be measured.

In some embodiments, the surface chemistry measuring apparatus may include an apparatus housing having an incident IR beam opening, a visible laser beam opening and a reflected IR beam opening; a processor in the apparatus housing; and an array of tunable laser infrared spectrometers in the apparatus housing and interfacing with the processor and the incident IR beam opening and the visible laser beam opening. The array of tunable infrared laser spectrometers may be configured for simultaneous measurement of surface chemistry across a surface to be measured using a range of infrared wavelengths. A visible laser in the apparatus housing may interface with the visible laser beam opening. A display may interface with the processor and may be adapted to display IR spectra of infrared wavelengths reflected from the surface to be measured.

The disclosure is further generally directed to a non-contact surface chemistry measurement method. An illustrative embodiment of the method includes providing a plurality of standards having a range of surface chemistry contamination; providing an array of tunable infrared laser spectrometers; obtaining infrared spectra of the range of surface chemistry contamination on the standards; calibrating the infrared spectra to the range of surface chemistry contamination; obtaining infrared spectra of a surface with potential contamination using the array of tunable infrared laser spectrometers; and comparing the infrared spectra of the surface with potential contamination with the infrared spectra of the range of surface chemistry contamination.

BRIEF DESCRIPTION OF THE ILLUSTRATIONS

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the invention and are not intended to limit the scope of the invention, which is defined by the claims. Furthermore, there is no intention to be bound by any expressed or implied theory presented in the preceding technical field, background, brief summary or the following detailed description.

Figure 1:
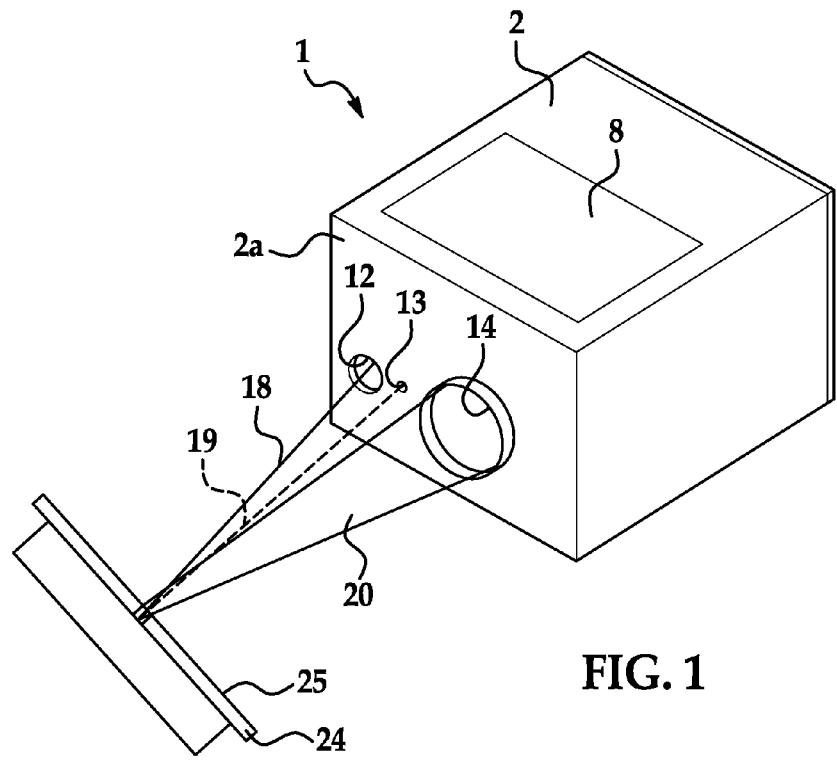
FIG. 1 is a perspective view of an illustrative embodiment of the non-contact surface chemistry measurement apparatus.
Figure 2:
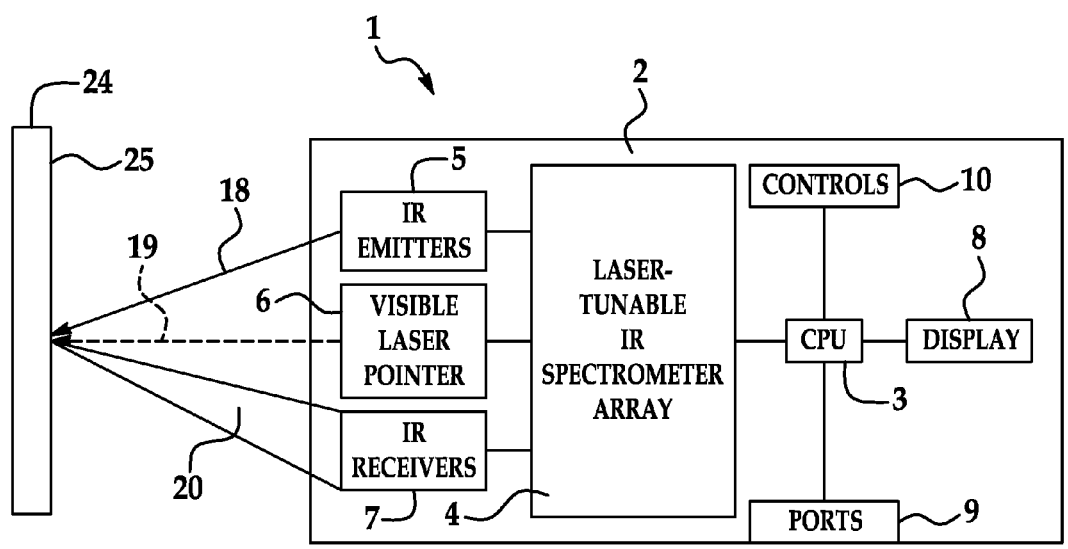
FIG. 2 is a schematic block diagram of an illustrative embodiment of the non-contact surface chemistry measurement apparatus.

Referring to FIGS. 1 and 2, an illustrative embodiment of a non-contact surface chemistry measurement apparatus, hereinafter apparatus, is generally indicated by reference numeral 1. The apparatus 1 may include an apparatus housing 2 which may contain at least some of the functional components of the apparatus 1. As shown in FIG. 1, a front housing plate 2a may be provided on the apparatus housing 2. An incident IR beam opening 12, a visible laser beam opening 13 and a reflected IR beam opening 14 may be provided in the front housing plate 2a. In some embodiments, the visible laser beam opening 13 may be generally between the incident IR beam opening 12 and the reflected IR beam opening 14, as further shown in FIG. 1.

As shown in FIG. 2, the apparatus 1 may include a CPU (Central Processing Unit) 3. A tunable IR laser spectrometer array 4 may interface with the CPU 3. The tunable IR laser spectrometer array 4 may be configured for simultaneous measurement across a surface to be measured 25 on a composite or other material 24 in a range of infrared wavelengths. The tunable IR laser spectrometer array 4 may include IR emitters 5. The IR emitters 5 may interface with the incident IR beam opening 12 (FIG. 1) provided in the front housing plate 2a. A visible laser pointer 6 may interface with the CPU 3. The visible laser pointer 6 may interface with the visible laser beam opening 13 provided in the front housing plate 2a. The tunable IR laser spectrometer array 4 may include IR receivers 7. The IR receivers 7 may interface with the reflected IR beam opening 14 provided in the front housing plate 2a of the apparatus housing 2. A display 8 may interface with the CPU 3. In some embodiments, the display 8 may be provided on the exterior of the apparatus housing 2, as shown in FIG. 1. At least one port 9, such as a USB port, for example and without limitation, may interface with the CPU 3. The port or ports 9 may be provided on the exterior of the apparatus housing 2. Controls 10 may interface with the CPU 3. In some embodiments, the controls 10 may be provided on the exterior surface of the apparatus housing 2. In some embodiments, the controls 10 may be provided in a touch screen format and may be incorporated into the display 8.

The visible laser pointer 6 may be adapted to emit a visible laser beam 19 through the visible laser beam opening 13

(FIG. 1) and against a selected area or spot, the surface chemistry or contamination of which to be measured, on the surface to be measured 25 of the material 24. The tunable IR laser spectrometer array 4 may be adapted to emit an incident IR beam 18 having a range of IR wavelengths from the IR emitters 5 through the incident IR beam opening 12 (FIG. 1) and against the selected area or spot on the surface to be measured 25. The IR receivers 7 may be adapted to receive a reflected IR beam 20 from the surface to be measured 25. In some embodiments, the IR emitters 5 may have the capability to emit the incident IR beam 18 and the IR receivers 7 may be adapted to collect the reflected IR beam 20 over all or portions of an operating wavelength range (e.g., 400 wavenumbers ($cm^{-1}$) to about 4000 wavenumbers ($cm^{-1}$)).

The CPU 3 may have the capability to process and store infrared spectra which correspond to the reflected IR beam 20 as well as display the spectra on the display 8. The CPU 3 may have the capability to perform mathematical manipulation of the data comprising the spectra including performing multivariate analysis of the spectra. The CPU 3 may be adapted to calibrate IR spectra obtained from standards having a range of surface contamination with the surface contamination on the standards. The CPU 3 may additionally have the capability to compare infrared spectra obtained from composite standards with infrared spectra obtained from a surface with potential contamination and display the comparison on the display 8. In some embodiments, the CPU 3 may have the capability to quantify the level of contamination on the measured surface and display the quantified level of contamination in numerical or other form on the display 8. An external device (not shown) may be connected to a port 9 on the apparatus housing 2 to facilitate uploading of data from the CPU 3 onto the external device.

In exemplary application of the apparatus 1, composite or other standards (not shown) having a range of silicone or other contamination on the surfaces of the standards may be prepared. In some applications, the standards may be graphite fiber epoxy composite standards. In other embodiments, the standards may include alternative materials. The tunable IR laser spectrometer array 4 of the apparatus 1 may emit an incident IR beam 18 against the surface of each standard. The visible laser pointer 6 may first emit a visible laser beam 19 against a selected area or point on the surface of each standard the level of contamination of which is to be measured to guide impingement of the incident IR beam 18 against the selected area or point on the surface. The IR receiver 7 may receive the reflected IR beam 20 which is reflected from the surface of each standard. The CPU 3 may process and store the IR spectrum obtained from the reflected IR beam 20 which corresponds to each standard. In some applications, a partial least squares (PLS) routine may be used to calibrate the IR spectra obtained from the standards to the amount of silicone contamination on the standards and verify the sensitivity of the measurement.

After calibration of the IR spectra obtained from the standards, the apparatus 1 may be operated to obtain infrared spectra of a surface to be measured 25 on a composite or other material 24. In some embodiments, the material 24 may have a metallic surface to be measured 25. In other embodiments, the material 24 may have a composite or other non-metallic surface to be measured 25. Accordingly, the tunable IR laser spectrometer array 4 of the apparatus 1 may emit an incident IR beam 18 against the surface to be measured 25. The visible laser pointer 6 may first emit a visible laser beam 19 against a selected area or point on the surface to be measured 25 to guide impingement of the incident IR beam 18 against the selected area or point on the surface to be measured 25. The IR receiver 7 may receive the reflected IR beam 20 which is reflected from the surface to be measured 25. The CPU 3 may process and store the IR spectrum obtained from the reflected IR beam 20 which corresponds to the surface to be measured 25. The CPU 3 may display the IR spectrum corresponding to the surface to be measured 25 along with the IR spectra corresponding to the standards. The CPU 3 may additionally compare the IR spectrum of the surface to be measured 25 to the IR spectra obtained from the silicone contamination standards. In some applications, the CPU 3 may quantify the level of contamination on the surface to be measured 25.

It will be appreciated by those skilled in the art that the apparatus 1 may provide access to chemical information on a variety of bonding surfaces including metal and composite bonding surfaces, for example and without limitation, with a rapid real-time measurement. The measurement may be implemented as an array of infrared wavelength segments that may be used to validate or verify various desired chemical species or lack of unwanted contaminant species on the surface of interest. The apparatus 1 facilitates non-contact measurement of a surface of interest with sufficient power to measure bonding surface chemistry, preventing the contamination of the surface which may otherwise occur through contact of IR instrumentation with the surface. The apparatus 1 may facilitate a rapid measurement method which provides full surface measurement coverage on large bonding surface areas. A simultaneous array of IR spectroscopy regions may provide access to measurement of a variety of contaminants and surface chemistries. It will be further appreciated by those skilled in the art that the method can be used to measure a thin coating on a surface without touching the coating or surface. This may be useful for bond primers on metals and composites in which it may be desired not to touch the surface for measurements but measurement of the bond primer thickness is desired (from about 0.2 to about 0.5 mils).

Figure 3:
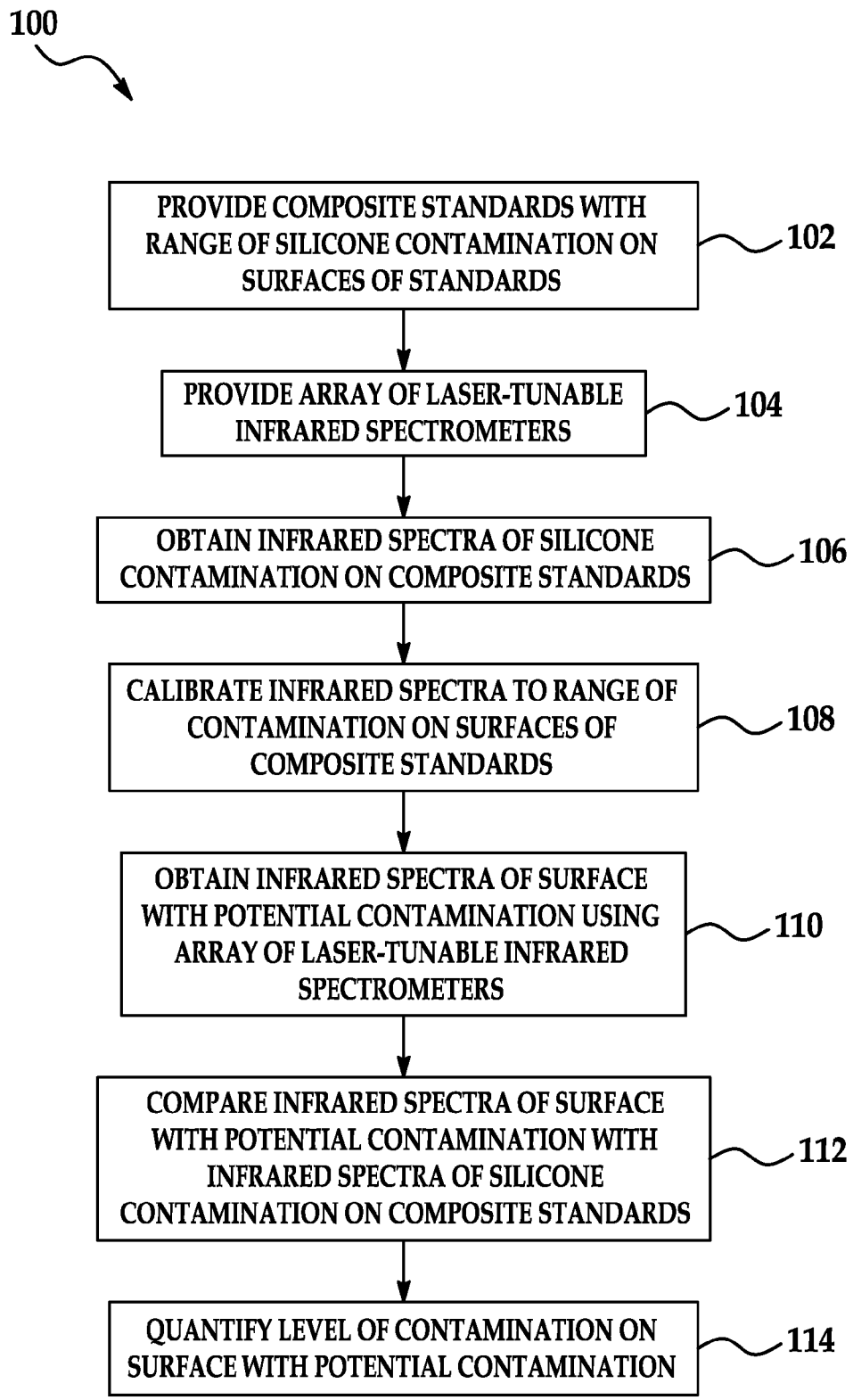
FIG. 3 is a flow diagram of an illustrative embodiment of a non-contact surface chemistry measurement method.

Referring next to FIG. 3, a flow diagram 100 of an illustrative embodiment of a non-contact surface chemistry measurement method is shown. In block 102, composite or other non-metallic or metallic standards with a range of silicone or other contamination on the surfaces of the standards are provided. In block 104, an array of tunable infrared laser spectrometers is provided. In block 106, infrared spectra of the silicone contamination on the composite standards is obtained. In some embodiments, infrared spectra using infrared wavelengths of from about 400 wavenumbers ($cm^{-1}$) to about 4000 wavenumbers is obtained. In block 108, the infrared spectra obtained in block 106 are calibrated to the range of contamination on the surfaces of the composite standards. In some embodiments, the infrared spectra may be calibrated to the range of contamination on the surfaces of the composite standards using a partial least squares (PLS) routine. In block 110, infrared spectra of a surface with potential silicone or other contamination is obtained using an array of tunable infrared laser spectrometers. In some embodiments, infrared spectra using infrared wavelengths of from about 400 wavenumbers ($cm^{-1}$) to about 4000 wavenumbers is obtained. In some embodiments, the surface with potential contamination may be metallic. In some embodiments, the surface with potential contamination may be composite or other non-metallic material. In block 112, the infrared spectra of the surface with potential contamination is compared to the infrared spectra of the standards. In block 114, the level of contamination on the surface with potential contamination is quantified.

Figure 4:
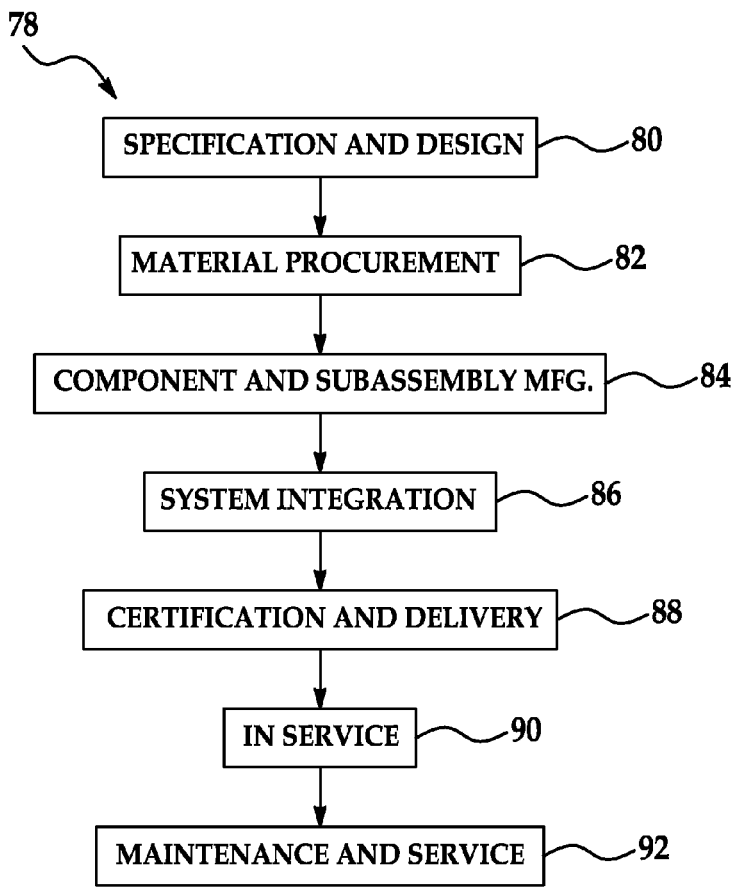
FIG. 4 is a flow diagram of an aircraft production and service methodology.
Figure 5:
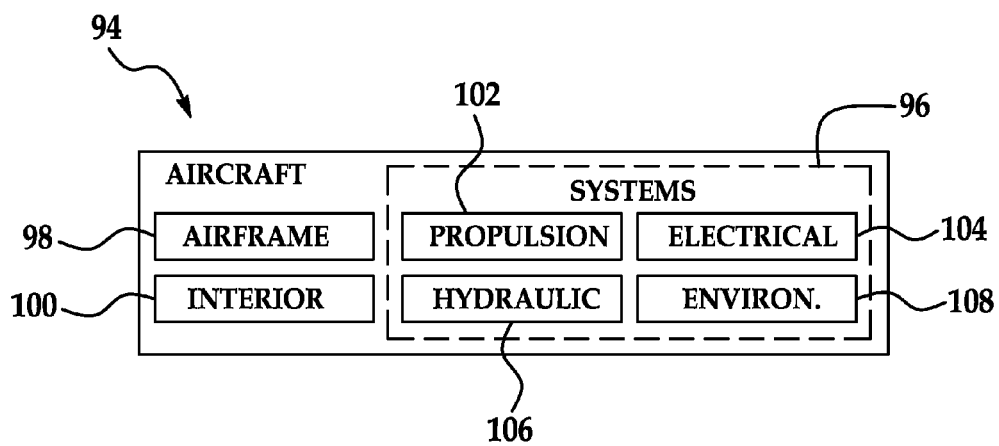
FIG. 5 is a block diagram of an aircraft.

Referring next to FIGS. 4 and 5, embodiments of the disclosure may be used in the context of an aircraft manufacturing and service method 78 as shown in FIG. 4 and an aircraft 94 as shown in FIG. 5. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 5, the aircraft 94 produced by exemplary method 78 may include an airframe 198 with a plurality of systems 196 and an interior 100. Examples of high-level systems 196 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A surface chemistry measuring apparatus, comprising:
   a processor;
   an array of tunable infrared laser spectrometers interfacing with said processor and configured for simultaneous measurement of surface chemistry across a surface to be measured using a range of infrared wavelengths, wherein the array of tunable infrared laser spectrometers is configured to emit an incident IR beam having a range of IR wavelengths through an incident IR beam opening and to receive a reflected IR beam having a range of IR wavelengths through a reflected IR beam opening; and
   a display interfacing with said processor and adapted to display IR spectra of infrared wavelengths reflected from said surface to be measured.

2. The apparatus of claim 1 further comprising a visible laser pointer interfacing with said processor.

3. The apparatus of claim 1 further comprising an apparatus housing and wherein said array of tunable infrared laser spectrometers is contained in said apparatus housing.

4. The apparatus of claim 3 wherein said incident IR beam opening is located in said housing.

5. The apparatus of claim 4 further comprising a visible laser beam opening in said apparatus housing and a visible laser pointer interfacing with said processor and interfacing with said visible laser beam opening.

6. The apparatus of claim 4 wherein said reflected IR beam opening is located in said housing.

7. The apparatus of claim 1 wherein said array of tunable infrared laser spectrometers is configured for simultaneous measurement of surface chemistry across a surface to be measured using infrared wavelengths of from about 400 wavenumbers ($cm^{-1}$) to about 4000 wavenumbers.

8. The apparatus of claim 1 further comprising at least one port interfacing with said processor.

9. A surface chemistry measuring apparatus, comprising:
   an apparatus housing having an incident IR beam opening, a visible laser beam opening and a reflected IR beam opening;
   a processor in said apparatus housing;
   an array of tunable infrared laser spectrometers in said apparatus housing and interfacing with said processor and said incident IR beam opening and said visible laser beam opening, wherein said array of tunable infrared laser spectrometers is configured to emit an incident IR beam having a range of IR wavelengths through said incident IR beam opening and to receive a reflected IR beam having a range of IR wavelengths through said reflected IR beam opening;
   said array of tunable infrared laser spectrometers configured for simultaneous measurement of surface chemistry across a surface to be measured using a range of infrared wavelengths;
   a visible laser in said apparatus housing and interfacing with said visible laser beam opening; and
   a display interfacing with said processor and adapted to display IR spectra of infrared wavelengths reflected from said surface to be measured.

10. The apparatus of claim 9 wherein said array of tunable infrared laser spectrometers is configured for simultaneous measurement of surface chemistry across a surface to be measured using infrared wavelengths of from about 400 wavenumbers ($cm^{-1}$) to about 4000 wavenumbers.

11. The apparatus of claim 9 further comprising at least one port interfacing with said processor.

12. The apparatus of claim 9 wherein said visible laser beam opening is generally between said incident IR beam opening and said reflected IR beam opening.

13. A non-contact surface chemistry measurement method, comprising:
   providing a plurality of standards having a range of surface chemistry contamination;
   providing an array of tunable infrared laser spectrometers;
   obtaining infrared spectra of said range of surface chemistry contamination on said standards by emitting an incident IR beam having a range of IR wavelengths through an incident IR beam opening and receiving a reflected IR beam having a range of IR wavelengths through a reflected IR beam opening;
   calibrating said infrared spectra to said range of surface chemistry contamination;
   obtaining infrared spectra of a surface with potential contamination using said array of tunable infrared laser spectrometers by emitting an incident IR beam having a range of IR wavelengths through the incident IR beam opening and receiving a reflected IR beam having a range of IR wavelengths through the reflected IR beam opening; and comparing said infrared spectra of said surface with potential contamination with said infrared spectra of said range of surface chemistry contamination.

14. The method of claim 13 further comprising quantifying a level of contamination on said surface with potential contamination.

15. The method of claim 13 wherein said obtaining infrared spectra of a surface with potential contamination using said array of tunable infrared laser spectrometers comprises obtaining infrared spectra of a metallic surface with potential contamination using said array of tunable infrared laser spectrometers.

16. The method of claim 13 wherein said obtaining infrared spectra of a surface with potential contamination using said array of tunable infrared laser spectrometers comprises obtaining infrared spectra of a non-metallic surface with potential contamination using said array of tunable infrared laser spectrometers.

17. The method of claim 16 wherein said obtaining infrared spectra of a non-metallic surface with potential contamination using said array of tunable infrared laser spectrometers comprises obtaining infrared spectra of a composite surface with potential contamination using said array of tunable infrared laser spectrometers.

18. The method of claim 13 wherein calibrating said infrared spectra to said range of surface chemistry contamination comprises calibrating said infrared spectra to said range of surface chemistry contamination using a partial least squares (PLS) routine.

19. The method of claim 13 wherein obtaining infrared spectra of a surface with potential contamination using said array of tunable infrared laser spectrometers comprises obtaining infrared spectra using infrared wavelengths of from about 400 wavenumbers ($cm^{-1}$) to about 4000 wavenumbers.

20. The method of claim 13 wherein obtaining infrared spectra of a surface with potential contamination using said array of tunable infrared laser spectrometers comprises obtaining infrared spectra of a surface with potential silicon contamination using said array of tunable infrared laser spectrometers.

* * * * *